(12) United States Patent
Pang et al.

(10) Patent No.: US 10,463,322 B2
(45) Date of Patent: Nov. 5, 2019

(54) METHOD AND APPARATUS FOR CONTROLLING SHAPE FILTER IN CT SCANNING DEVICE

(71) Applicant: Shenyang Neusoft Medical Systems Co., Ltd., Shenyang (CN)

(72) Inventors: Ling Pang, Shenyang (CN); Junlong Han, Shenyang (CN); Shanshan Lou, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 959 days.

(21) Appl. No.: 14/836,982

(22) Filed: Aug. 27, 2015

(65) Prior Publication Data

US 2016/0058400 A1 Mar. 3, 2016

(30) Foreign Application Priority Data

Aug. 29, 2014 (CN) .......................... 2014 1 0437450

(51) Int. Cl.
  *A61B 6/00* (2006.01)
  *A61B 6/03* (2006.01)
(52) U.S. Cl.
  CPC ............ *A61B 6/4035* (2013.01); *A61B 6/032* (2013.01); *A61B 6/542* (2013.01); *A61B 6/547* (2013.01)
(58) Field of Classification Search
  CPC ....... A61B 1/4021; A61B 1/4035; G21K 1/04
  See application file for complete search history.

(56) References Cited

U.S. PATENT DOCUMENTS

| | | | | |
|---|---|---|---|---|
| 6,028,908 A * | 2/2000 | Taguchi | ................. | A61B 6/032 378/15 |
| 7,068,750 B2 * | 6/2006 | Toth | ....................... | A61B 6/032 378/156 |
| 7,474,736 B2 * | 1/2009 | Munro | ..................... | G21K 1/10 378/159 |
| 9,349,494 B2 * | 5/2016 | Roessl | ................... | A61B 6/032 |

(Continued)

FOREIGN PATENT DOCUMENTS

| | | |
|---|---|---|
| CN | 102271587 A | 12/2011 |
| CN | 103124520 A | 5/2013 |

(Continued)

OTHER PUBLICATIONS

Machine English translation of JP 2007319340.*

(Continued)

*Primary Examiner* — Dani Fox
*Assistant Examiner* — Soorena Kefayati
(74) *Attorney, Agent, or Firm* — Kilpatrick Townsend & Stockton LLP (57) ABSTRACT

The disclosure includes: judging whether a center line of an object to be scanned is deviated from a rotation axis of a gantry of a CT scanning device; determining a first distance by which the center line of the object to be scanned is deviated from the rotation axis in a case that the center line of the object to be scanned is deviated from the rotation axis; determining according to the first distance a second distance by which the shape filter is to be translated in each projection angle; and controlling the shape filter to make it translate by the second distance in each corresponding projection angle.

10 Claims, 6 Drawing Sheets

(56) References Cited

U.S. PATENT DOCUMENTS

| | | | |
|---|---|---|---|
| 2001/0007585 A1* | 7/2001 | Nukui | A61B 6/032 378/8 |
| 2003/0058994 A1 | 3/2003 | Sembritzki | |
| 2005/0013411 A1* | 1/2005 | Yahata | A61B 6/06 378/156 |
| 2005/0089136 A1* | 4/2005 | Toth | A61B 6/032 378/16 |
| 2010/0166138 A1* | 7/2010 | Yan | A61B 6/032 378/4 |
| 2011/0261923 A1 | 10/2011 | Schmitt et al. | |
| 2012/0012742 A1* | 1/2012 | Ren | A61B 6/035 250/252.1 |
| 2012/0105525 A1* | 5/2012 | Leung | B41J 2/0057 347/9 |
| 2013/0058451 A1* | 3/2013 | Hsieh | A61B 6/032 378/16 |
| 2013/0182820 A1* | 7/2013 | Proksa | A61B 6/032 378/8 |
| 2014/0211912 A1* | 7/2014 | Wang | A61B 6/5205 378/19 |
| 2015/0297155 A1* | 10/2015 | Christensen | A61B 6/032 378/5 |
| 2015/0305698 A1* | 10/2015 | Katchalski | A61B 6/032 378/19 |
| 2015/0313569 A1* | 11/2015 | Stevens | A61B 6/032 378/8 |
| 2016/0174917 A1* | 6/2016 | Koehler | A61B 6/4035 378/158 |

FOREIGN PATENT DOCUMENTS

| | | | | |
|---|---|---|---|---|
| JP | 2002052019 A | | 2/2002 | |
| JP | 2006075339 | * | 3/2006 | |
| JP | 2006075339 A | | 3/2006 | |
| JP | 2007319340 | * | 12/2007 | A61B 6/03 |
| JP | 2007319340 A | | 12/2007 | |
| WO | 2010/079393 A1 | | 7/2010 | |
| WO | 2012/042484 A1 | | 4/2012 | |

OTHER PUBLICATIONS

English translation of JP 2006075339 (Year: 2006).*
The First Office Action dated Dec. 30, 2016 regarding the Chinese priority patent application (Appl.No. 201410437450.7).

* cited by examiner

METHOD AND APPARATUS FOR CONTROLLING SHAPE FILTER IN CT SCANNING DEVICE

The present application claims the priority to Chinese Patent Applications No. 201410437450.7, titled "METHOD AND APPARATUS FOR CONTROLLING SHAPE FILTER IN CT SCANNING DEVICE", filed with the Chinese State Intellectual Property Office on Aug. 29, 2014, which is incorporated herein by reference in its entirety.

BACKGROUND

Figure 1:
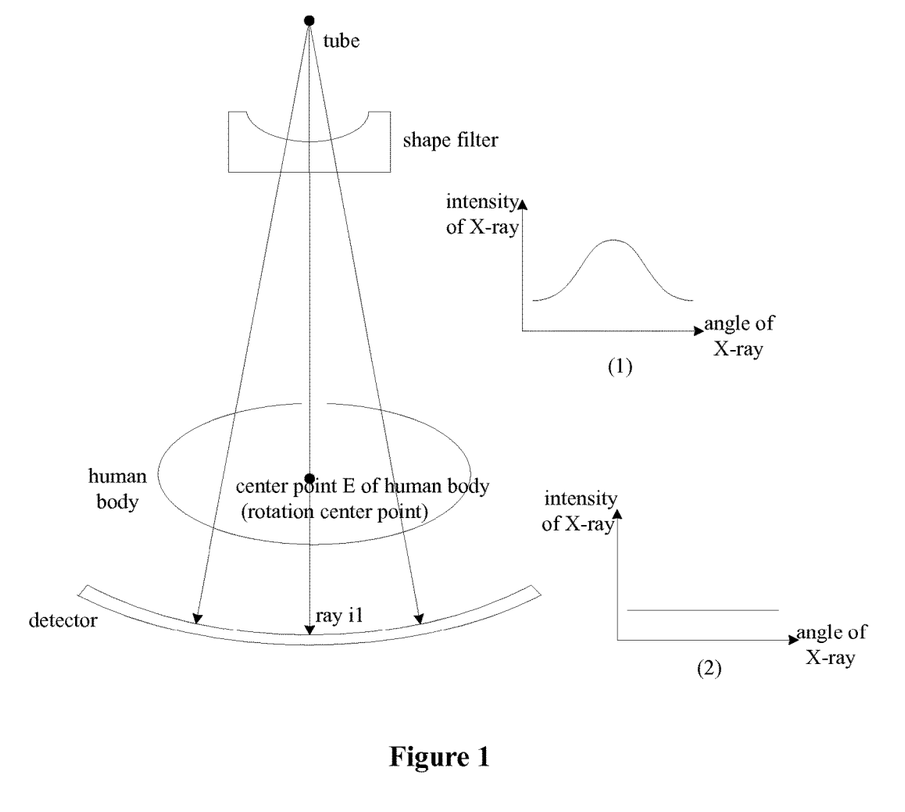
FIG. 1 is a schematic diagram of a placement of an object to be scanned in an ideal condition.

A Computed Tomography (CT) device includes components such as a tube, a shape filter and a detector. The tube, the shape filter and the detector can rotate around the rotation axis of the gantry of the CT device, and the position of the rotation axis is fixed. Reference is made to FIG. 1 which illustrates a schematic diagram of a placement of an object to be scanned on a scanning plane. In the conventional CT scanning, the center line of the object to be scanned, i.e., of the human body, is at the rotation axis, in a case that the human body is not in the off-center position. Since the section of the human body is in a shape like an ellipse, the attenuation of X-ray emitted by the tube after passing through the human body is different in a case that there is no shape filter, and the noise of the rebuilt image may be not consistent. In view of this, a shape filter is provided between the tube and the human body, and the X-ray passes through the shape filter firstly and then passes through the human body. Under a certain projection angle of the X-ray, the intensity of each ray in the fan beam formed by X-rays passing through the shape filter is as shown by (1) in FIG. 1 in a case that the human body is not in an off-center position. It can be seen that, since the length that the central ray i1 travels in the shape filter is shortest, the intensity of the central ray i1 after passing through the shape filter is strongest; and the intensity of the rays on both sides of the central ray i1 gradually decreases as the rays leave farther from the central ray i1, because the length that the rays travels in the shape filter gradually increases as the rays leave farther from the central ray i1. Furthermore, the central ray i1 passes through the intersection of the center line of the human body and the scanning plane, i.e., the center point E of the human body, thus the path in which the ray with the strongest intensity (which aims at the center point of the human body) in the fan beam passes through the human body is the longest, and the path in which the ray with the weaker intensity on each side of the central ray i1 passes through the human body is shorter. Therefore, the intensity of the rays received by the detector is substantially the same, which is approximate to a horizontal, as shown by (2) in FIG. 1. In this case, more uniform dose of scanning is received by different parts of the human body, that is, the intensity of the ray which passes through the wider part of the section of the human body is stronger and the intensity of the ray which passes through the narrower part of the section of the human body is weaker, and thereby the total dose of scanning is reduced and the consistency of the image noise among various parts of a patient is improved (the noise is directly proportional to the intensity of the X-ray received by the detector).

Figure 2:
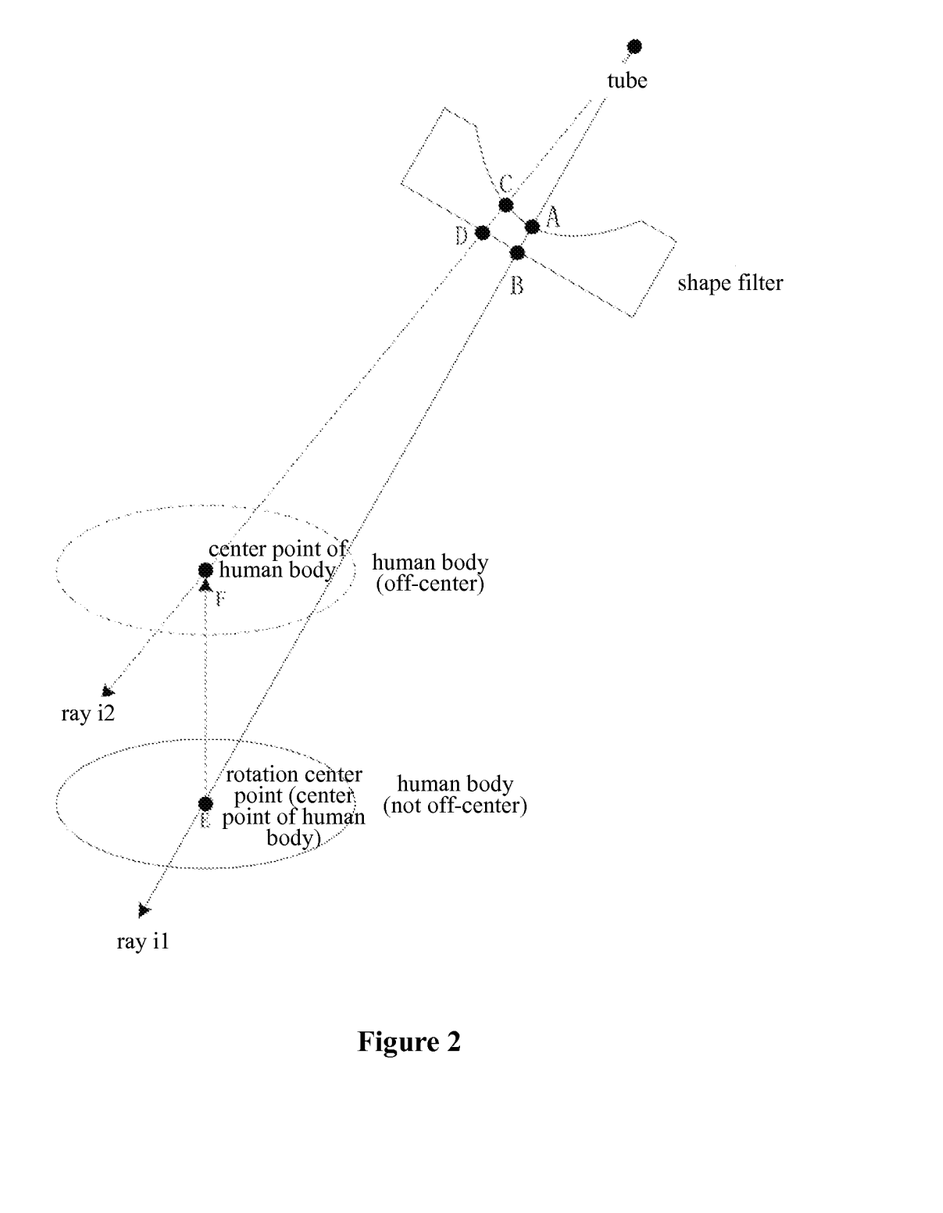
FIG. 2 is a schematic diagram of a placement of an object to be scanned in a case that the object to be scanned is in an off-center position.

Reference is made to FIG. 2 which illustrates another schematic diagram of a placement of an object to be scanned on a scanning plane. The center point of the object to be scanned, i.e., of the human body, is moved from the intersection of the rotation axis and the scanning line, i.e., the rotation center point E to the point F (in a perpendicular direction as shown in FIG. 2) in a case that the human body is in an off-center position. In this case, the ray i2 passing through the center point of the human body is not the ray i1 with the strongest intensity in fan beam (because the length of the line segment CD is not the shortest). Therefore, the dose of scanning received by different parts of the human body may not be uniform, and thereby the noise of the scan image is not consistent.

DETAILED DESCRIPTION

During a CT scanning, if the object to be scanned is in the off-center position and the position of the shape filter is not changed accordingly, the dose of scanning received by different parts of the object to be scanned (the human body) may be not uniform, and thereby the noise of the scan image is not consistent. In view of this, in the example of the disclosure, in a case that the object to be scanned is in the off-center position, the shape filter is moved according to the deviation of the object to be scanned, so that the ray with the strongest intensity after passing through the shape filter passes through the center line of the object to be scanned. Therefore, more uniform dose of scanning is received by different parts of the object to be scanned, and thereby the consistency of the noise of the scan image is improved while the total dose of scanning is efficiently reduced.

Figure 3:
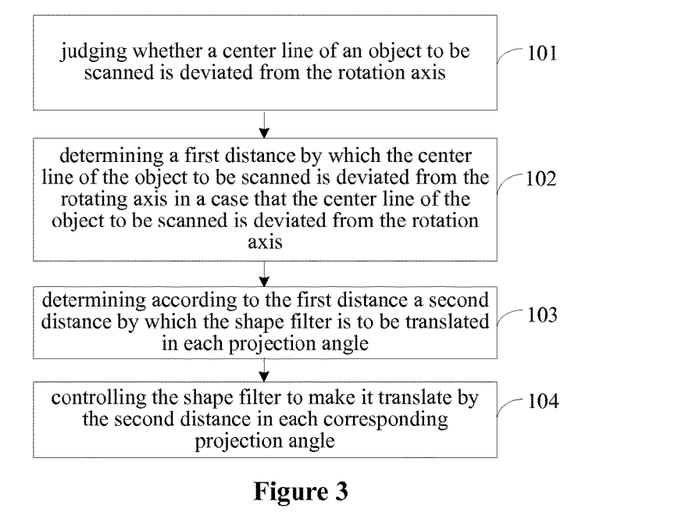
FIG. 3 is a flowchart of a method for controlling a shape filter in a CT scanning device according to an embodiment of the disclosure.

Reference is made to FIG. 3 which is a flowchart of a method for controlling a shape filter in a CT scanning device according to an example of the disclosure. The CT scanning device includes a tube, the shape filter and a detector. The tube and the detector are able to rotate around a rotation axis of a gantry of the CT scanning device, and the shape filter is able to be translated relative to the tube. The method is usually performed by a processor of the CT scanning device. The method includes blocks 101 to 104.

Block 101, it is judged whether a center line of the object to be scanned is deviated from the rotation axis of the gantry of the CT scanning device.

In the block, judging whether the center line of the object to be scanned is deviated from the rotation axis of the gantry of the CT scanning device may include:

performing lateral film scanning on the object to be scanned to obtain a scan result; determining a channel of the detector corresponding to a ray passing through the center line of the object to be scanned according to the scan result; and judging whether a distance between the determined channel of the detector and a central channel of the detector is less than a preset threshold, determining that the center line of the object to be scanned is not deviated from the rotation axis of the gantry of the CT scanning device in a case that the distance between the determined channel of the detector and the central channel of the detector is less than the preset threshold or determining that the center line of the object to be scanned is deviated from the rotation axis of the gantry of the CT scanning device in a case that the distance between the determined channel of the detector and the central channel of the detector is not less than the preset threshold.

Figure 4:
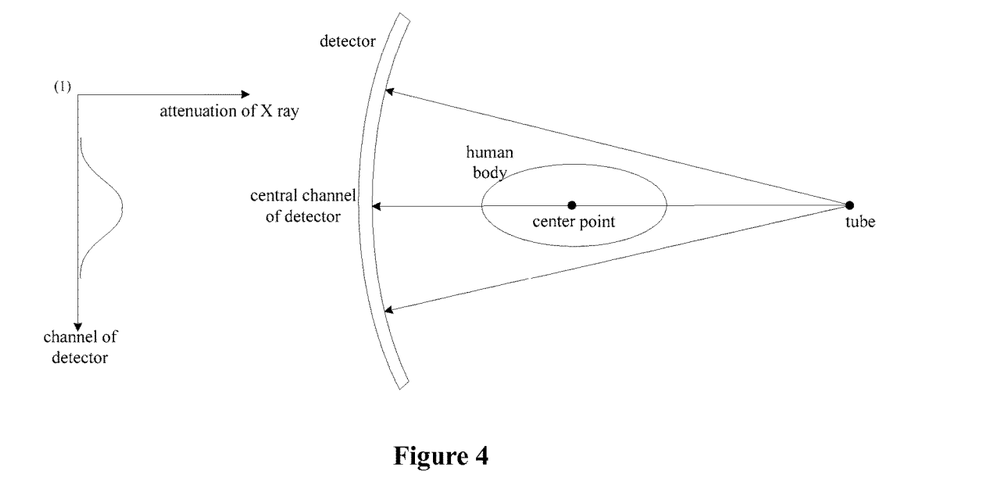
FIG. 4 is a schematic diagram of a lateral film scanning of an object to be scanned in a case that the object is in an ideal condition according to an embodiment of the disclosure.

In the example of the disclosure, it may be judged whether the center line of the object to be scanned is deviated from the rotation axis, and the plain film scanning data obtained after the plain film scanning may be used to judge whether the center line of the object to be scanned is deviated from the rotation axis. In an example of the disclosure, the scan result of the lateral film scanning of the object to be scanned is used to judge whether the center line of the object to be scanned is deviated from the rotation axis in the perpendicular direction. Reference is made to FIG. 4, the lateral film scanning of the object to be scanned is to scan the human body from a side of the human body. The attenuated X-ray is received by the detector and an attenuation curve (as shown by (1) in FIG. 4) of the X-ray after passing through the human body is obtained according to the data received by the detector. The channel of the detector corresponding to the ray passing through the center line of the human body may be determined based on the data of the attenuation curve. In a case that the center line of the human body is not deviated from the rotation axis of the gantry of the CT scanning device, the ray passing through the center line of the human body is emitted to the center of the detector and is received by the central channel of the detector, with some human position error being permitted in practice. Therefore, it is determined that the center line of the human body is not deviated from the rotation axis in the perpendicular direction if the distance between the channel of the detector corresponding to the ray passing through the center line of the human body and the central channel of the detector is less than a preset threshold, or otherwise it is determined that the center line of the human body is deviated from the rotation axis in the perpendicular direction. It should be noted that there are many ways for judging whether the center line of the object to be scanned is deviated from the rotation axis, which is not limited herein.

Based on the above-mentioned lateral film scanning, it is further described below how to determine the channel of the detector corresponding to the ray passing through the center line of the human body based on the data of the attenuation curve.

In the lateral film scanning of the human body, M lateral sections of the human body are selected and the attenuation data of the X-rays after passing through the M lateral sections are obtained. The attenuated rays after passing through the lateral sections are collected by N channels of the detector, and the CT raw data collected by the detector rawdata=$\{p_{00}, p_{01}, p_{02}, \ldots, p_{ij}, \ldots\}$, i=0, 1, 2, 3, ..., M−1, j=0, 1, 2, 3 ..., N−1 are obtained after being processed, where each piece of data in rawdata represents the attenuation amplitude of the X-ray.

In an example of the disclosure, the following M×N pieces of data are collected firstly:

$$\text{rawdata} = \{p_{00}, p_{01}, p_{02}, \ldots, p_{ij}, \ldots\}, i=0,1,2,3, \ldots, M-1, j=0,1,2,3 \ldots, N-1$$

The $X_m$-th channel of the detector corresponding to the ray passing through the center line of the object to be scanned is then calculated according to the following formula:

$$X_m = \frac{\sum_{i,j} p_{ij} \cdot j}{\sum_{i,j} p_{ij}} \quad (1)$$

where M is the number of lateral sections selected for the object to be scanned, N is the number of channels of the detector, and $p_{ij}$ is a value representing the intensity of the ray passing through the i-th lateral section and collected by the j-th channel of the detector.

Block 102, a first distance by which the center line of the object to be scanned is deviated from the rotation axis is determined in a case that the center line of the object to be scanned is deviated from the rotation axis.

Figure 5:
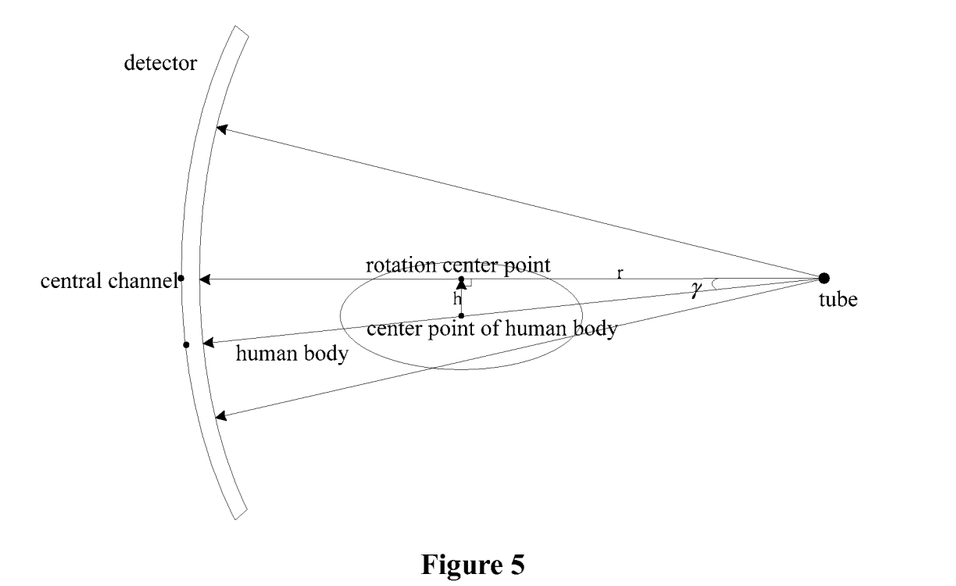
FIG. 5 is a schematic diagram of a lateral film scanning of an object to be scanned in a case that the object is in an off-center position according to an embodiment of the disclosure.

In an example of the disclosure, the position of the shape filter may not be adjusted in a case that the center line of the object to be scanned is not deviated from the rotation axis. The first distance h by which the center line of the human body is deviated from the rotation axis in the perpendicular direction is usually calculated according to the scan result of the lateral film scanning, in a case that the center line of the object to be scanned is deviated from the rotation axis. Reference is made to FIG. 5 which illustrates another schematic diagram of the lateral film scanning according to an example of the disclosure. The center line of the human body is deviated from the rotation axis, and the number of channels by which the channel of the detector corresponding to the ray passing through the center line of the human body is deviated from the central channel of the detector is:

$$X_m - \frac{N-1}{2}$$

where $X_m$ may be obtained according to formula (1), N is the number of channels of the detector, and the angle γ by which the human body is off-center (i.e., the angle between the ray passing through the rotation axis and the ray passing through the center line of the human body) is:

$$\gamma = \frac{X_m - \frac{N-1}{2}}{N} \cdot \beta \quad (2)$$

where β is a fan angle formed by all channels of the detector and the tube.

Given that a rotation radius (the vertical distance from the tube to the rotation axis) is r, the vertical distance h by which the center line of the human body is deviated from the rotation axis is:

$$h = r \cdot \tan\gamma = r \cdot \tan\left(\frac{X_m - \frac{N-1}{2}}{N} \cdot \beta\right) \quad (3)$$

In view of the above, in the example of the disclosure, the first distance by which the center line of the object to be scanned is deviated from the rotation axis in the perpendicular direction is determined in a case that the center line of the object to be scanned is deviated from the rotation axis. Specifically, the first distance h may be calculated according to the following formula:

$$h = r \cdot \tan\left(\frac{X_m - \frac{N-1}{2}}{N} \cdot \beta\right),$$

where r is the vertical distance from the tube to the rotation axis of the gantry of the CT scanning device, $X_m$ is the channel of the detector corresponding to the ray passing through the center line of the object to be scanned, N is the number of channels of the detector, and β is a fan angle formed by all channels of the detector and the tube.

Block 103, a second distance by which the shape filter is to be translated in each projection angle is determined according to the first distance, during scanning the object to be scanned.

Figure 6:
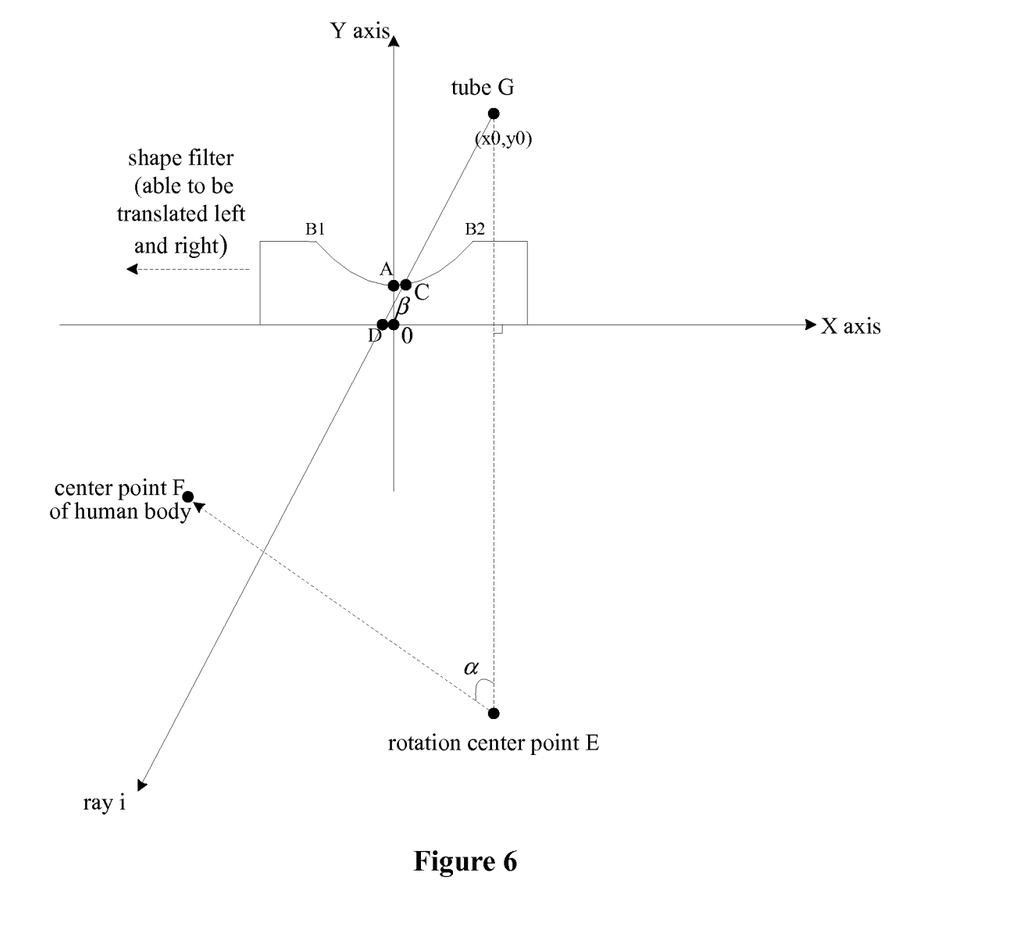
FIG. 6 is a schematic diagram of translation of a shape filter in a CT scanning device according to an embodiment of the disclosure.

In the disclosure, the shape filter is usually controlled to be translated in a case that the center line of the object to be scanned is deviated from the rotation axis. It should be understood that, the vertical distance between the tube and the shape filter is not changed in the translation, and the shape filter is only translated left and right relative to the tube. In an example, the shape filter in FIG. 2 needs to be translated to the top-left (translated left relative to the tube), so that the ray i2 after passing through the shape filter is the ray with the strongest intensity in the fan beam. Reference is made to FIG. 6 which illustrates a schematic diagram of translation of the shape filter. In a case that the shape filter is translated to a certain position, there is a ray i with the strongest intensity after passing through the shape filter in the fan beam, and the path in which the ray i travels in the shape filter is the shortest. The translation of the shape filter is controlled to stop if the ray i just passes through the center point F of the human body. Therefore, by continually translating the shape filter, a position at which the ray i passes through the center point F of the human body is found, and this position is the correct position of the shape filter in the current view (the projection angle of the X-ray).

How to obtain the translation distance $x_0$ of the shape filter is described below in details.

In an example of FIG. 6, on the scanning plane which is perpendicular to the rotation axis and is through the tube, the position o at the bottom of the shape filter which corresponds to the center of the shape filter (the lowest point A) is set as the origin of coordinates. In this case, the coordinates of the tube are $(x_0, y_0)$, where $x_0$ is the distance by which the shape filter is translated left relative to the tube currently, and $y_0$ is the vertical distance (which is fixed) between the tube and the bottom of the shape filter. The angle of the current view (the projection angle of the X-ray) is α (i.e., the angle between the connection line GE connecting the tube and the rotation center point and the connection line EF connecting the center point of the human body and the rotation center point, where the rotation center point is the intersection of the rotation axis and the scanning plane and the center point of the object to be scanned is an intersection of the center line of the object to be scanned and the scanning plane). The rotation radius |EG|=r is a constant which is related to the scanning device, and the coordinates of the rotation center point E are $(x_0, y_0-r)$. The distance by which the center point F of the human body is deviated from the rotation center point E in the perpendicular direction is |EF|=h which may be obtained according to the above-mentioned formula (3). If the equation of the arc B1B2 of the shape filter in the coordinate axes XY is:

$$y=f(x) \quad (4)$$

and given that the slope of the ray i (the ray which passes through the shape filter in the shortest path) is k, the linear equation of the ray i is:

$$\frac{y - y_0}{x - x_0} = k \quad (5)$$

where k is the slope of the linear equation of the ray i.

The position of the ray i in the shape filter is obtained firstly, and a point C is the intersection point of the ray i and the arc of the shape filter. The coordinates of the point C can be obtained by simultaneous equations of formulas (4) and (5) as follows:

$$\begin{cases} y = f(x) \\ \frac{y - y_0}{x - x_0} = k \end{cases} \quad (6)$$

The Coordinates $(x_1, y_1)$ of the Point C are Obtained from the Simultaneous Equations (6), where $$y_1 = y_1(k, x_0) \quad (7)$$

The length of the line segment CD may be obtained as follows if the angle between the line segment CD and the positive direction of X axis is β:

$$|CD| = \frac{y_1(k, x_0)}{\sin\beta} = y_1(k, x_0) \cdot \frac{\sqrt{k^2 + 1}}{k} \quad (8)$$

The slope k is obtained by minimizing the length of the line segment CD:

$$|CD| = \min \Rightarrow k = k(x_0) \quad (9)$$

That is, the slope of the ray i with the strongest intensity in the fan beam after passing through the shape filter is $k(x_0)$, after the shape filter is translated by $x_0$ from the original position.

It is required that the ray i passes through the center point F of the human body as mentioned above. In view of this, it is required that $k(x_0)$ is equal to the slope of the connection line between the tube G and the center point F of the human body, i.e., $$k(x_0) = k_{GF} \quad (10)$$

Given that the coordinates of the center point F of the human body are $(x_2, y_2)$ and the coordinates of the rotation center point E are $(x_0, y_0-r)$, the distance by which the center point F of the human body is deviated from the rotation center point E in the perpendicular direction is |EF|=h, then:

$$\begin{cases} x_2 = x_0 - h \cdot \sin\alpha \\ y_2 = (y_0 - r) + h \cdot \cos\alpha \end{cases} \quad (11)$$

The slope of GF can be obtained as follows after the coordinates of F are obtained:

$$k_{GF} = \frac{y_2 - y_0}{x_2 - x_0} = \frac{-r + h \cdot \cos\alpha}{-h \cdot \sin\alpha} \quad (12)$$

The distance $x_0$ by which the shape filter is to be translated can be obtained by substituting formula (12) into formula (10).

Based on the above, the second distance $x_0$ can be obtained according to the following formula in the disclosure:

$$k(x_0) = \frac{-r + h \cdot \cos\alpha}{-h \cdot \sin\alpha},$$

where h is the first distance, r is a vertical distance from the tube to the rotation axis, a is an angle between a first connection line and a second connection line, the first connection line is a connection line between the tube and the rotation center point, the second connection line is a connection line between the center point of the object to be scanned and the rotation center point, and $k(x_0)$ is a slope function of the ray with the strongest intensity after passing through the shape filter, $x_0$ is a variable in the slope function.

A method for determining the slope function includes: transforming a formula $$|CD| = y_1(k, x_0) \cdot \frac{\sqrt{k^2 + 1}}{k}$$

after minimizing |CD| to obtain the slope function $k=k(x_0)$, where |CD| is a length that the ray travels in the shape filter, and $y_1(k, x_0)$ is a longitudinal coordinate of an intersection point between the ray and an arc of the shape filter.

Block 104, the shape filter is controlled to be translated by the second distance in each corresponding projection angle, so that more uniform dose of scanning is received by the object to be scanned as compared with that before the translation.

It should be noted that the shape filter moves relative to the tube in the scanning, that is, the second distance by which the shape filter is to be translated changes as the change of the projection angle in the scanning That is, for each projection angle, it is necessary to determine a second distance in the projection angle and control the shape filter to make it translate by the second distance in the projection angle, so that more uniform dose of scanning is received by the object to be scanned as compared with that before the translation and thereby the consistency of the noise of the scan image is improved. For this purpose, after the translation of the shape filter, the ray with the strongest intensity after passing through the shape filter passes through the center line of the object to be scanned.

According to the method for controlling a shape filter in a CT scanning device provided by the disclosure, the shape filter is controlled to be translated if it is determined that the center line of the object to be scanned is deviated from the rotation axis, so that the ray with the strongest intensity after passing through the shape filter passes through the center line of the object to be scanned after translation of the shape filter. Therefore, more uniform dose of scanning is received by different parts of the object to be scanned, and thereby the consistency of the noise of the scan image is improved while the total dose of scanning is efficiently reduced.

Figure 7:
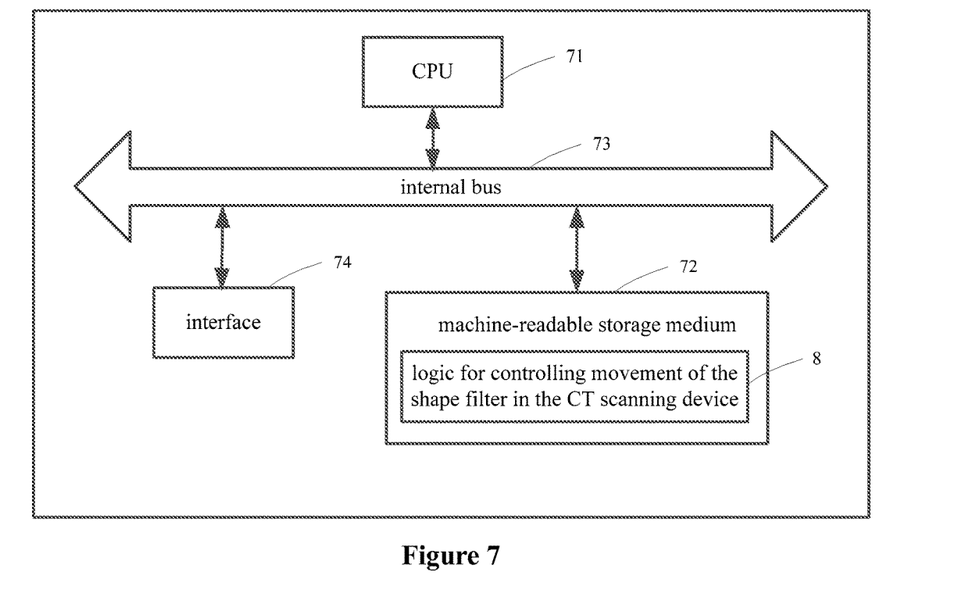
FIG. 7 is a hardware architecture diagram of an apparatus for controlling translation of a shape filter in a CT scanning device according to an embodiment of the disclosure.

Corresponding to the above method, the disclosure further provides an apparatus for controlling a shape filter in a CT scanning device. The CT scanning device includes a tube, the shape filter and a detector, and the tube and the detector are able to rotate around a rotation axis of a gantry of the CT scanning device. In the disclosure, the apparatus may be integrated into a console of the CT scanning device, or may be on a separate computing device. In different examples, the apparatus may be embodied as software, or hardware, or combination of software and hardware. Reference is made to FIG. 7, in an example of the disclosure, the apparatus includes a central processing unit (CPU) 71 and a machine-readable storage medium 72, and the CPU 71 and the machine-readable storage medium 72 are connected with each other through an internal bus 73. In other possible implementation, the apparatus may further include an external interface 74 for communicating with other device or component.

In different examples, the machine-readable storage medium 72 may be Random Access Memory (RAM), volatile memory, nonvolatile memory, flash memory, memory driver (for example, hard disk drive), solid state disk, memory disc of any type (for example, optical disk, DVD), other similar storage medium and any combination thereof.

Figure 8:
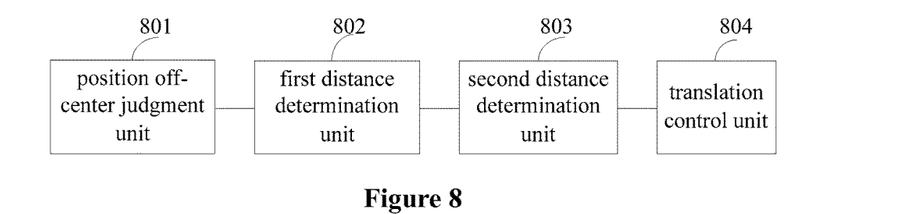
FIG. 8 is a diagram of functional modules for controlling translation of a shape filter in a CT scanning device according to an embodiment of the disclosure.

In addition, the logic 8 for controlling translation of the shape filter is stored on the machine-readable storage medium 72. The logic 8 is configured to control the shape filter to make it translate left or right relative to the tube. As shown in FIG. 8, in view of function, the logic 8 for controlling translation of the shape filter in the CT scanning device includes:

an off-center position judgment unit 801 configured to judge whether a center line of an object to be scanned is deviated from a rotation axis of a gantry of the CT scanning device;

a first distance determination unit 802 configured to determine a first distance by which the center line of the object to be scanned is deviated from the rotation axis in a case that the center line of the object to be scanned is deviated from the rotation axis;

a second distance determination unit 803 configured to determine according to the first distance a second distance by which the shape filter is to be translated in each projection angle; and a translation control unit 804 configured to control the shape filter to make it translate by the second distance in each corresponding projection angle.

The off-center position judgment unit 801 includes:

a plain film scanning module configured to perform lateral film scanning on the object to be scanned to obtain a scan result;

a channel determination module configured to determine a channel of the detector corresponding to a ray passing through the center line of the object to be scanned according to the scan result; and an off-center judgment module configured to judge whether a distance between the determined channel of the detector and a central channel of the detector is less than a preset threshold, determine that the center line of the object to be scanned is not deviated from the rotation axis in a case that the distance between the determined channel of the detector and the central channel of the detector is less than the preset threshold or determine that the center line of the object to be scanned is deviated from the rotation axis in a case that the distance between the determined channel of the detector and the central channel of the detector is not less than the preset threshold.

It is described in the following, by taking software implementation as an example, how the apparatus controlling translation of the shape filter executes the logic 8. In the example, the logic 8 in the disclosure should be understood as computer instructions stored in the machine-readable storage medium 72. The CPU 71 in the apparatus in the disclosure executes, by reading the machine-readable storage medium 72, instructions of functional modules corresponding to the logic 8 to:

judge whether a center line of an object to be scanned is deviated from a rotation axis of a gantry of the CT scanning device;

determine a first distance by which the center line of the object to be scanned is deviated from the rotation axis in a case that the center line of the object to be scanned is deviated from the rotation axis;

determine according to the first distance a second distance by which the shape filter is to be translated in each projection angle; and control the shape filter to make it translate by the second distance in each corresponding projection angle.

The CPU 71 further executes, by reading the machine-readable storage medium 72, instructions of functional modules corresponding to the logic 8 to:

perform lateral film scanning on the object to be scanned to obtain a scan result;

determine a channel of the detector corresponding to a ray passing through the center line of the object to be scanned according to the scan result; and judge whether a distance between the determined channel of the detector and a central channel of the detector is less than a preset threshold, determining that the center line of the object to be scanned is not deviated from the rotation axis in a case that the distance between the determined channel of the detector and the central channel of the detector is less than the preset threshold or determining that the center line of the object to be scanned is deviated from the rotation axis in a case that the distance between the determined channel of the detector and the central channel of the detector is not less than the preset threshold.

The CPU 71 further executes, by reading the machine-readable storage medium 72, instructions of functional modules corresponding to the logic 8 to:

collect M×N pieces of data as follows, where M is the number of lateral sections selected for the object to be scanned, N is the number of channels of the detector:

rawdata={$p_{00}, p_{01}, p_{02}, \ldots, p_{ij}, \ldots$}, $i=0,1,2,3,\ldots,M-1, j=0,1,2,3\ldots,N-1$, where $p_{ij}$ is a value representing intensity of a ray passing through the i-th lateral section and collected by the j-th channel of the detector;

then calculate the $X_m$-th channel of the detector corresponding to the ray passing through the center line of the object to be scanned according to the following formula:

$$X_m = \frac{\sum_{i,j} p_{ij} \cdot j}{\sum_{i,j} p_{ij}}.$$

The CPU 71, for determining the first distance by which the center line of the object to be scanned is deviated from the rotation axis in a perpendicular direction, further executes, by reading the machine-readable storage medium 72, instructions of functional modules corresponding to the logic 8 to:

calculate the first distance h according to the following formula:

$$h = r \cdot \tan\left(\frac{X_m - \frac{N-1}{2}}{N} \cdot \beta\right),$$

where r is a vertical distance from the tube to the rotation axis, $X_m$ is the channel of the detector corresponding to the ray passing through the center line of the object to be scanned, N is the number of channels of the detector, and β is a fan angle formed by all channels of the detector and the tube.

The CPU 71, for determining the second distance that the shape filter is to be translated, further executes, by reading the machine-readable storage medium 72, instructions of functional modules corresponding to the logic 8 to:

obtain the second distance $x_0$ according to the following formula:

$$k(x_0) = \frac{-r + h \cdot \cos\alpha}{-h \cdot \sin\alpha},$$

where h is the first distance, r is a vertical distance from the tube to the rotation axis, α is an angle between a first connection line and a second connection line, the first connection line is a connection line between the tube and the rotation center point and the second connection line is a connection line between the center point of the object to be scanned and the rotation center point, where the rotation center point is an intersection of the rotation axis and the scanning plane, the center point of the object to be scanned is an intersection of the center line of the object to be scanned and the scanning plane, and the scanning plane is a plane which is perpendicular to the rotation axis and is through the tube, and $k(x_0)$ is a slope function of a ray with the strongest intensity after passing through the shape filter, $x_0$ is a variable in the slope function.

The slope function is determined by:
transforming a formula $$|CD| = y_1(k, x_0) \cdot \frac{\sqrt{k^2+1}}{k}$$

after minimizing |CD| to obtain the slope function $k=k(x_0)$, where |CD| is a length that the ray travels in the shape filter, and $y_1(k, x_0)$ is a longitudinal coordinate of an intersection point between the ray and an arc of the shape filter.

It can be seen from the above examples that according to the apparatus for controlling a shape filter in a CT scanning device provided by the disclosure, the shape filter is controlled to be translated if it is determined that the object to be scanned is in an off-center position, so that the ray with the strongest intensity after passing through the shape filter passes through the center point of the object to be scanned after translation of the shape filter. Therefore, more uniform dose of scanning is received by different parts of the object to be scanned, and thereby the consistency of the noise of the scan image is improved while the total dose of scanning is efficiently reduced.

It should be understood that in the disclosure, relational terms such as "first" and "second" are used only to distinguish one entity or operation from another entity or operation, but not necessarily demand or imply that there is an actual relation or order among those entities and operations. In addition, the terms "including", "comprising", or any other variations thereof means a non-exclusive inclusion, so that the process, method, article or device that includes a series of elements includes not only these elements but also other elements that are not explicitly listed, or further includes elements inherent in the process, method, article or device. Moreover, if there is no further limitation, the element defined by the wording "comprise(s) a . . . " does not exclude the case that the process, method, article or device including the element also includes other same elements.

The description of the examples herein enables those skilled in the art to implement or use the disclosure. Numerous modifications to the examples will be apparent to those skilled in the art, and the general principle herein can be implemented in other examples without deviation from the spirit or scope of the present disclosure. Therefore, the present disclosure is not limited to the examples described herein, but in accordance with the widest scope consistent with the principle and novel features disclosed herein.

What is claimed is:

1. A method for controlling a shape filter in a CT scanning device, wherein the CT scanning device comprises a tube, the shape filter and a detector, the tube and the detector are able to rotate around a rotation axis of a gantry of the CT scanning device, and the shape filter is able to be translated relative to the tube, and wherein the method comprises:
   judging whether a center line of an object to be scanned is deviated from the rotation axis;
   determining a first distance by which the center line of the object to be scanned is deviated from the rotation axis in a case that the center line of the object to be scanned is deviated from the rotation axis;
   determining, according to the first distance, a second distance by which the shape filter is to be translated in each projection angle; and
   controlling the shape filter to make it translate by the second distance in each corresponding projection angle,
   wherein determining according to the first distance the second distance by which the shape filter is to be translated comprises:
   obtaining the second distance $x_0$ according to the following formula:

$$k(x_0) = \frac{-r + h \cdot \cos\alpha}{-h \cdot \sin\alpha},$$

wherein r is a vertical distance from the tube to the rotation axis, h is the first distance; α is an angle between a first connection line and a second connection line, the first connection line is a connection line between the tube and a rotation center point and the second connection line is a connection line between a center point of the object to be scanned and the rotation center point, wherein the rotation center point is an intersection of the rotation axis and a scanning plane, the center point of the object to be scanned is an intersection of the center line of the object to be scanned and the scanning plane, and the scanning plane is a plane which is perpendicular to the rotation axis and is through the tube; and $k(x_0)$ is a slope function of a ray with the strongest intensity after passing through the shape filter, $x_0$ is a variable in the slope function.

2. The method according to claim 1, wherein judging whether the center line of the object to be scanned is deviated from the rotation axis comprises:
   performing lateral film scanning on the object to be scanned to obtain a scan result;
   determining a channel of the detector corresponding to a ray passing through the center line of the object to be scanned according to the scan result; and
   judging whether a distance between the determined channel of the detector and a central channel of the detector is less than a preset threshold, determining that the center line of the object to be scanned is not deviated from the rotation axis in a case that the distance between the determined channel of the detector and the central channel of the detector is less than the preset threshold or determining that the center line of the object to be scanned is deviated from the rotation axis in a case that the distance between the determined channel of the detector and the central channel of the detector is not less than the preset threshold.

3. The method according to claim 2, wherein determining the channel of the detector corresponding to the ray passing through the center line of the object to be scanned according to the scan result comprises:
   collecting M×N pieces of data as follows:

rawdata={$p_{00}, p_{01}, p_{02}, \ldots, p_{ij}, \ldots$},$i$=0,1,2, 3,...,$M$−1,$j$=0,1,2,3...,$N$−1; and calculating the $X_m$-th channel of the detector corresponding to the ray passing through the center line of the object to be scanned according to the following formula:

$$X_m = \frac{\sum_{i,j} p_{ij} \cdot j}{\sum_{i,j} p_{ij}},$$

wherein M is the number of lateral sections selected for the object to be scanned, N is the number of channels of the detector, and $p_{ij}$ is a value representing intensity of a ray passing through the i-th lateral section and collected by the j-th channel of the detector.

4. The method according to claim 3, wherein determining the first distance by which the center line of the object to be scanned is deviated from the rotation axis comprises: determining the first distance by which the center line of the object to be scanned is deviated from the rotation axis in a perpendicular direction; and
   determining the first distance by which the center line of the object to be scanned is deviated from the rotation axis in the perpendicular direction comprises:
   calculating the first distance h according to the following formula:

$$h = r \cdot \tan\left(\frac{X_m - \frac{N-1}{2}}{N} \cdot \beta\right),$$

wherein $X_m$ is the channel of the detector corresponding to the ray passing through the center line of the object to be scanned, N is the number of channels of the detector, and β is a fan angle formed by all channels of the detector and the tube.

5. The method according to claim 4, wherein the slope function is determined by:
transforming a formula $$|CD| = y_1(k, x_0) \cdot \frac{\sqrt{k^2 + 1}}{k}$$

after minimizing |CD| to obtain the slope function k=k($x_0$), wherein |CD| is a length that the ray travels in the shape filter, and $y_1$(k, $x_0$) is a longitudinal coordinate of an intersection point between the ray and an arc of the shape filter.

6. An apparatus for controlling a shape filter in a CT scanning device, wherein the apparatus is configured to control the shape filter to make it translate relative to a tube of the CT scanning device, the CT scanning device comprises the tube, the shape filter and a detector, the tube and the detector are able to rotate around a rotation axis of a gantry of the CT scanning device, and wherein the apparatus comprises:
a central processing unit (CPU) and a machine-readable storage medium, the CPU and the machine-readable storage medium are connected with each other through an internal bus, and the CPU executes by reading the machine-readable storage medium instructions corresponding to a logic for controlling translation of the shape filter to:
judge whether a center line of an object to be scanned is deviated from the rotation axis;
determine a first distance by which the center line of the object to be scanned is deviated from the rotation axis in a case that the center line of the object to be scanned is deviated from the rotation axis;
determine, according to the first distance, a second distance by which the shape filter is to be translated in each projection angle; and
control the shape filter to make it translate by the second distance in each corresponding projection angle,
wherein the CPU, for determining the second distance, further executes by reading the machine-readable storage medium instructions corresponding to the logic for controlling translation of the shape filter to:
obtain the second distance $x_0$ according to the following formula:

$$k(x_0) = \frac{-r + h \cdot \cos\alpha}{-h \cdot \sin\alpha},$$

wherein r is a vertical distance from the tube to the rotation axis, h is the first distance; α is an angle between a first connection line and a second connection line, the first connection line is a connection line between the tube and a rotation center point and the second connection line is a connection line between a center point of the object to be scanned and the rotation center point, wherein the rotation center point is an intersection of the rotation axis and a scanning plane, the center point of the object to be scanned is an intersection of the center line of the object to be scanned and the scanning plane, and the scanning plane is a plane which is perpendicular to the rotation axis and is through the tube; and k($x_0$) is a slope function of a ray with the strongest intensity after passing through the shape filter, $x_0$ is a variable in the slope function.

7. The apparatus according to claim 6, wherein the CPU further executes by reading the machine-readable storage medium instructions corresponding to the logic for controlling translation of the shape filter to:
perform lateral film scanning on the object to be scanned to obtain a scan result;
determine a channel of the detector corresponding to a ray passing through the center line of the object to be scanned according to the scan result; and
judge whether a distance between the determined channel of the detector and a central channel of the detector is less than a preset threshold, determining that the center line of the object to be scanned is not deviated from the rotation axis in a case that the distance between the determined channel of the detector and the central channel of the detector is less than the preset threshold or determining that the center line of the object to be scanned is deviated from the rotation axis in a case that the distance between the determined channel of the detector and the central channel of the detector is not less than the preset threshold.

8. The apparatus according to claim 7, wherein the CPU further executes by reading the machine-readable storage medium instructions corresponding to the logic for controlling translation of the shape filter to:
collect M×N pieces of data as follows:

rawdata={$p_{00},p_{01},p_{02},\ldots,p_{ij},\ldots$},i=0,1,2,3,$\ldots$,M−1,j=0,1,2,3$\ldots$,N−1, wherein M is the number of lateral sections selected for the object to be scanned, N is the number of channels of the detector, and $p_{ij}$ is a value representing intensity of a ray passing through the i-th lateral section and collected by the j-th channel of the detector; and
calculate the $X_m$-th channel of the detector corresponding to the ray passing through the center line of the object to be scanned according to the following formula:

$$X_m = \frac{\sum_{i,j} p_{ij} \cdot j}{\sum_{i,j} p_{ij}}.$$

9. The apparatus according to claim 8, wherein the CPU, for determining the first distance by which the center line of the object to be scanned is deviated from the rotation axis in a perpendicular direction, further executes by reading the machine-readable storage medium instructions corresponding to the logic for controlling translation of the shape filter to:
calculate the first distance h according to the following formula:

$$h = r \cdot \tan\left(\frac{X_m - \frac{N-1}{2}}{N} \cdot \beta\right),$$

wherein $X_m$ is the channel of the detector corresponding to the ray passing through the center line of the object to be scanned, N is the number of channels of the detector, and $\beta$ is a fan angle formed by all channels of the detector and the tube.

10. The apparatus according to claim 9, wherein the slope function is determined by:
transforming a formula $$|CD| = y_1(k, x_0) \cdot \frac{\sqrt{k^2 + 1}}{k}$$

after minimizing |CD| to obtain the slope function $k=k(x_0)$, wherein |CD| is a length that the ray travels in the shape filter, and $y_1(k, x_0)$ is a longitudinal coordinate of an intersection point between the ray and an arc of the shape filter.

* * * * *